US00PP37808P2

(12) United States Plant Patent
Nishikawa

(10) Patent No.: US PP37,808 P2
(45) Date of Patent: Oct. 20, 2026

(54) ***DELOSPERMA* PLANT NAMED 'FS 21-254'**

(50) Latin Name: *Delosperma nubigenum*
Varietal Denomination: FS 21-254

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 19/640,401

(22) Filed: Apr. 6, 2026

(30) Foreign Application Priority Data

Nov. 18, 2025 (QZ) ..... PBR 2025/2396

(51) Int. Cl.
*A01H 6/00* (2018.01)
*A01H 5/02* (2018.01)

(52) U.S. Cl.
USPC ..... Plt./422

(58) Field of Classification Search
USPC ..... Plt./263.1, 422
See application file for complete search history.

(56) References Cited

U.S. PATENT DOCUMENTS

2024/0341211 P1 * 10/2024 Nishikawa ..... A01H 6/14
Plt./442

* cited by examiner

*Primary Examiner* — Karen M Redden
(74) *Attorney, Agent, or Firm* — Penny J. Aguirre

(57) ABSTRACT

A new cultivar of *Delosperma nubigenum* plant named 'FS 21-254' that is characterized by its flowers with a high quantity of petals resulting in a full and multi-layered effect, especially in spring, its vibrant red flowers with white and yellow centers, its long flowering period: blooming continuously from early summer into autumn, its floriferous blooming habit, its compact, prostrate, and densely branched plant habit, its ease of growing with no need for vernalization, and its high tolerance to heat, drought, and humidity.

2 Drawing Sheets

Botanical classification: *Delosperma nubigenum*
Variety denomination: 'FS 21-254'.

CROSS-REFERENCE TO RELATED APPLICATIONS

This application claims priority to European Community Plant Variety Office (CPVO) Plant Breeder's Rights Application No. 2025/2396 filed on Nov. 18, 2025, under 35 U.S.C. 119(f), the entire contents of which is incorporated by reference herein. The Applicant received the information for the Plant Breeders' Rights Application directly from the Inventor. This application is co-pending with a U.S. Plant Patent Application filed for plants derived from the same breeding program that is entitled *Delosperma* Plant Named 'T21-248' (U.S. Plant patent application Ser. No. 19/640,393).

BACKGROUND OF THE INVENTION

The present invention relates to a new and distinct cultivar of *Delosperma* plant, botanically known as *Delosperma nubigenum* 'FS 21-254' and will be referred to hereinafter by its cultivar name, 'FS 21-254'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall goal of the breeding program was to develop new cultivars of *Delosperma* plants with flowers with many petals (double), floriferous blooming habits, compact and neat plant habits, and heat resistance.

'FS 21-254' was selected in the Inventor's trial garden in 2019 as a single unique plant from amongst the seedlings derived from a cross made in 2018 between unnamed and unpatented plants from the Inventor's breeding program.

Asexual propagation of the new cultivar was first accomplished by stem cuttings in July of 2019 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'FS 21-254' as a unique cultivar of *Delosperma*.

1. 'FS 21-254' exhibits flowers with a high quantity of petals resulting in a full and multi-layered effect, especially in spring.
2. 'FS 21-254' exhibits vibrant red flowers with white and yellow centers.
3. 'FS 21-254' exhibits a long flowering period: blooming continuously from early summer into autumn.
4. 'FS 21-254' exhibits a floriferous blooming habit.
5. 'FS 21-254' exhibits a compact, prostrate, and densely branched plant habit.
6. 'FS 21-254' exhibits ease of growing with no need for vernalization.
7. 'FS 21-254' exhibits a high tolerance to heat, drought, and humidity.

The parent plants of 'FS 21-254' are both similar to 'FS 21-254' in growth habit. The parent plants of 'FS 21-254' both differ from 'FS 21-248' in having flowers with fewer petals. 'FS 21-254' can be most closely compared to the *Delosperma* cultivars 'WOWD20111' (U.S. Plant Pat. No. 25,684) and 'S3red' (U.S. Plant Pat. No. 36,246). 'WOWD20111' is similar to 'FS 21-254' in flower size and in being suitable for growing in small containers. 'WOWD20111' differs from 'FS 21-254' in having flowers with fewer petals that are yellow in color and a less dense and less compact growth habit with longer internodes. 'S3red' is similar to 'FS 21-254' in having an abundance of flowers that are similar in color. 'S3red' differs from 'FS 21-254' in having flowers with fewer petals (especially in spring) and suitability for growing in even smaller pots (P12 versus P15).

'FS 21-254' can also be compared to the co-pending cultivar of *Delosperma nubigenum* 'FS 21-248'. 'FS 21-248' is similar to 'FS 21-254' in growth and blooming habits and in having flowers with many petals. 'FS 21-248' differs from 'FS 21-254' in having flowers with vibrant magenta-colored petals.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Concept Plants, Quality Cuttings, Plantipp, and FlorSAIKA.

BRIEF DESCRIPTION OF THE DRAWINGS

The accompanying color photographs illustrate the overall appearance and distinct characteristics of the new *Delosperma*. The photographs were taken of a 5-month-old plant of the new cultivar as grown outdoors in a 14-cm container in Sabaudia, Italy.

The photograph in FIG. 1 provides a top view of 'FS 21-254' in bloom.

Figure 1:
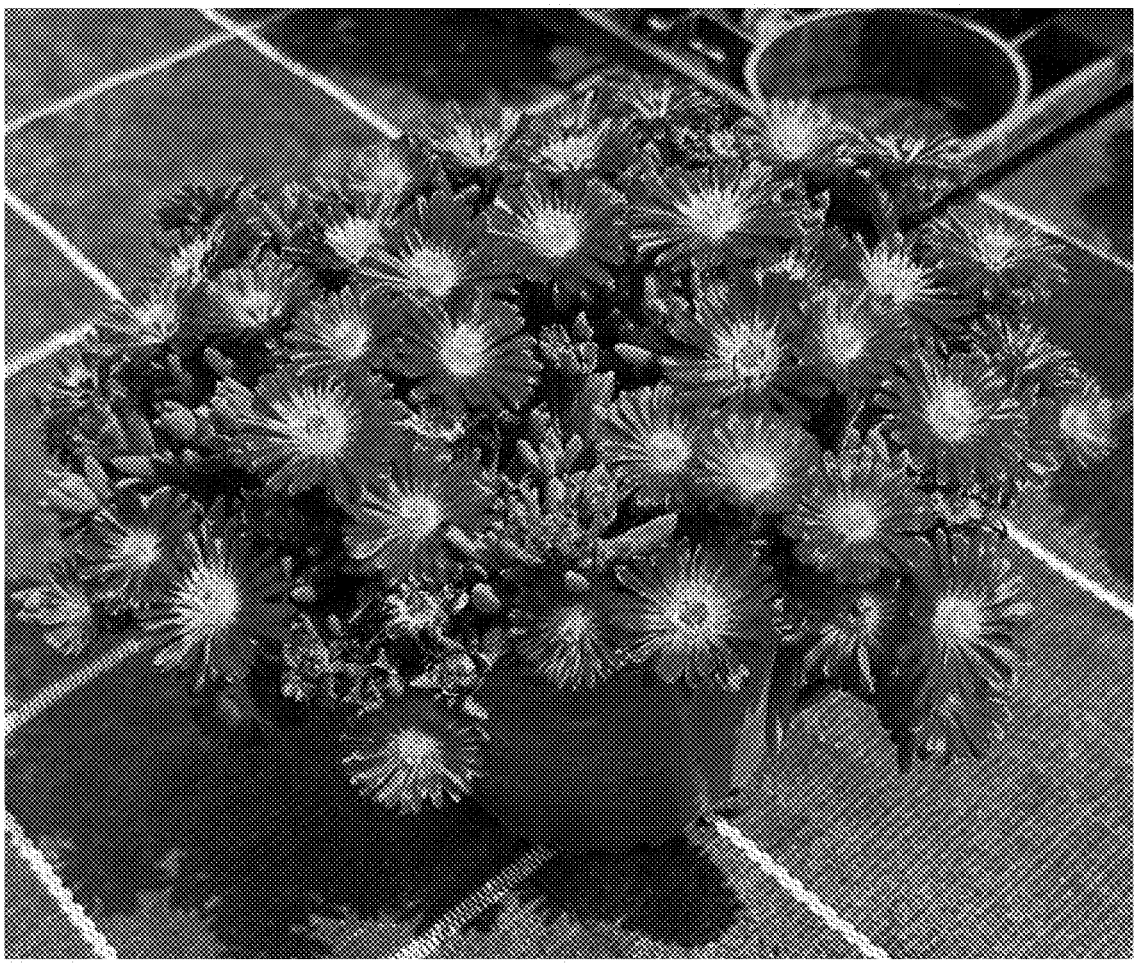
Figure 2:
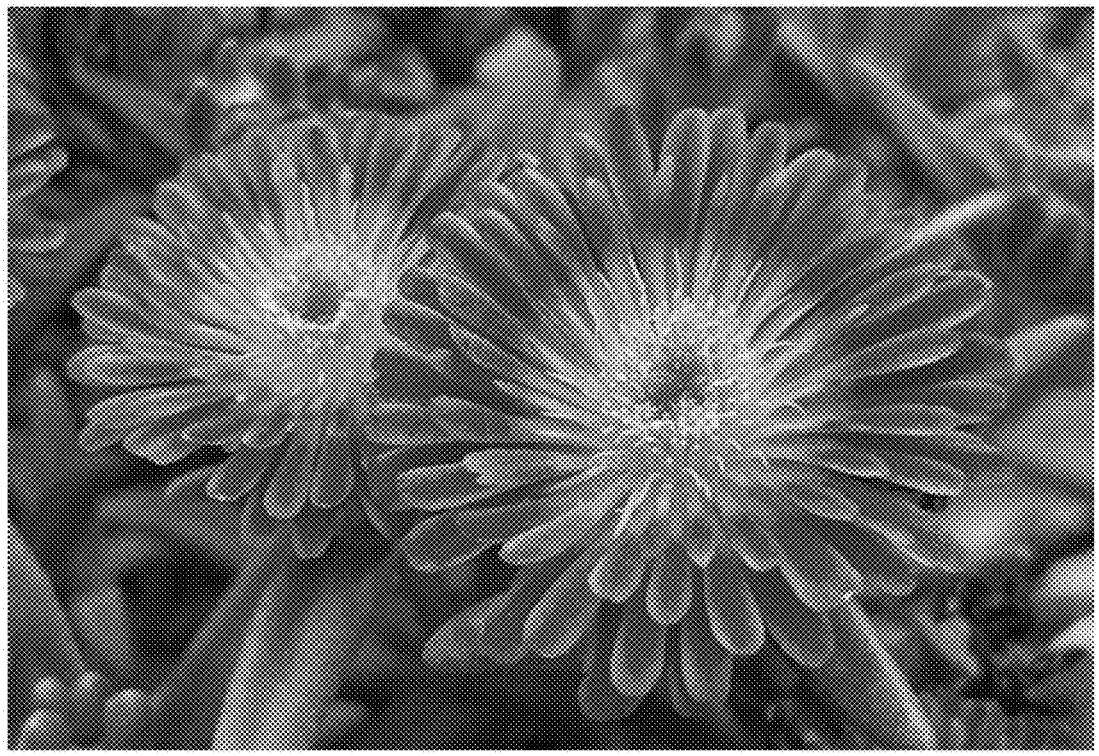

The photograph in FIG. 2 provides a close-up view of the flowers of 'FS 21-254'.

The colors in the photographs are as close as possible with the digital photography and printing techniques utilized and the color codes in the detailed botanical description accurately describe the new *Delosperma*.

DETAILED BOTANICAL DESCRIPTION

The following is a detailed description of 5-month-old plants of the new cultivar as grown outdoors in 17-cm pots in Waddinxveen, the Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early summer to early autumn in The Netherlands.

*Plant type*.—Evergreen perennial.

*Plant habit*.—Dense, compact, flattened, prostrate.

*Height and spread*.—Reaches an average of 21 cm in height and 34 cm in width as a 5-month-old plant grown in a container.

*Cold hardiness*.—Observed to be hardy to at least U.S.D.A. Zone 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a plug to young plant in a P9 container.

*Growth habit*.—Moderate.

Stem description:

*Shape*.—Round.

*Stem color*.—144B to 144C and 183A.

*Stem size*.—Lateral branches; an average of 8 cm in length and 3 mm in diameter.

*Internode length*.—2 cm to 3 cm.

*Stem substance*.—Succulent.

*Stem surface*.—Moderately glossy, moderately pubescent.

*Branching habit*.—Densely branched; basal and lateral branches.

Foliage description:

*Leaf shape*.—Ligulate.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface*.—Both surfaces slightly glossy, sparsely to moderately pubescent.

*Leaf color*.—137A and 145B.

*Leaf size*.—Up to 4 cm in length and 6 mm in width.

*Leaf quantity*.—10 per lateral branch.

*Leaf attachment*.—Sessile.

Inflorescence description:

*Inflorescence type*.—Flowers solitary, terminal.

*Flower number*.—2 per lateral stem.

*Flower fragrance*.—None.

*Flower aspect*.—Outward to upright.

*Flower longevity*.—4 days, self-cleaning.

*Flower type*.—Single.

*Flower size*.—Average of 3.7 cm in diameter and 1 cm in depth.

*Flower buds*.—Broadly ovate to oblong in shape, an average of 1 cm in length and 7 mm in diameter, 33A in color, surface is smooth.

*Calyx*.—Rotate in shape, average of 7 mm in depth and 2.4 cm in diameter.

*Sepals*.—5, rotate, ovate in shape, margin entire, an average of 1 cm in length and 5 mm in width, broadly acute apex, broadly cuneate base, surface is smooth and dull, both surfaces 137B and 145A in color.

*Petals*.—70 to 80 per flower, produces more petals in spring, rotate and slightly curved downward, oblanceolate in shape, surface is moderately glossy on both surfaces and smooth, margin entire, apex obtuse, base cuneate, an average of 1.5 cm in length, 2 mm in width, color; upper surface opening 34A to 34B, upper surface when fully open N34A to N34B, center and base 21B and NN155A, lower surface opening and fully open 60C to 60D, center and base NN155A and 21B.

*Petaloids*.—An average of 30 to 40 per flower, rotate and near vertical surrounding stamens, lanceolate in shape, glossy on both surfaces, margin entire, apex obtuse, base truncate, an average of 4 mm in length and 1 mm in width, color; both surfaces opening and fully open 7B, tips sometimes lightly flushed with N34A to N34B.

*Peduncle*.—Average of 2.7 cm in length and 3 mm in diameter, straight on top of lateral branch at 0° to vertical, 145A in color, surface moderately glossy and slightly pubescent.

*Pedicel*.—None.

Reproductive organs:

*Pistils*.—5, an average of 2 mm in length, stigma; triangular in shape, style and stigma; (not distinguishable) combined an average of 2 mm in length, 151A in color, ovary; 143C in color.

*Stamens*.—Average of 60, anthers; dorsifixed and narrowly oblong in shape, 3 mm in length, 0.5 mm in diameter, 10D in color, filaments; 3 mm in length, NN155A in color, pollen; moderate in quantity and 6C in color.

*Fruit and seed*.—Fruit and seed production has not observed under the conditions tested.

It is claimed:

1. A new and distinct variety of *Delosperma* plant named 'FS 21-254' as described and illustrated herein.

* * * * *